United States Patent
Bayston et al.

(10) Patent No.: US 6,207,854 B1
(45) Date of Patent: Mar. 27, 2001

(54) PREPARATION OF 3-AMINO-3-CYCLOPROPYLPROPANOATE ESTERS

(75) Inventors: Daniel John Bayston, Oxfordshire; Virginie Falque, Reading; Ronald Michael Scott, Oxfordshire, all of (GB)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/465,188

(22) Filed: Dec. 15, 1999

(51) Int. Cl.$^7$ .................. C07C 69/74; C07C 229/00; C07B 57/00
(52) U.S. Cl. .................. 560/124; 560/155; 562/401; 562/402; 562/506; 562/553
(58) Field of Search .................. 560/124, 155; 562/401, 402, 506, 553

(56) References Cited

U.S. PATENT DOCUMENTS

| 3,433,791 | 3/1969 | Bentley . |
| 3,474,101 | 10/1969 | Bentley . |
| 4,863,918 | 9/1989 | Gala et al. . |
| 5,344,957 | * | 9/1994 | Bovy et al. .................. 560/35 |

FOREIGN PATENT DOCUMENTS

| 279821 | 7/1995 | (CZ) . |
| 0380312 | 8/1990 | (EP) . |
| 539110 | 12/1984 | (ES) . |
| WO9304047 | 3/1993 | (WO) . |
| WO9307867 | 4/1993 | (WO) . |

OTHER PUBLICATIONS

Chemical Abstracts definition of "3–cyclopropylalanine".*
Lazar, L. et al "A simple synthesis of beta–substituted beta–amino acids" Synth. Comm., vol. 28, No. 2, pp. 219–224, 1998.*
Suffness, Ed., Taxol® Science and Applications (CRC, Boca Raton, FL, 1995) and Plattner in Annual Reports in Medicinal Chemistry (Academic Press, San Diego, 1994), vol. 29, pp 113–22.

* cited by examiner

*Primary Examiner*—Howard C. Lee
*Assistant Examiner*—Leigh C. Maier
(74) *Attorney, Agent, or Firm*—Michael J. Blake; Harry J. Gwinnell

(57) ABSTRACT

Disclosed a process for preparing substantially enantiomerically pure 3-amino-3-cyclopropylpropanoate esters, i.e., esters of 3-amino-3-cyclopropylpropanoic acid (3-cyclopropylalanine esters or 3-CPA esters) by a 5-step process wherein cyclopropanecarboxaldehyde (CPCA) is reacted with malonic acid and a source of ammonia to obtain 3-cyclopropylalanine (3-CPA); esterifying the 3-CPA; contacting the 3-CPA ester with a substantially enantiomerically pure acid selected from tartaric acid, dibenzoyltartaric acid and mandelic acid to obtain a diastereomeric salt of the 3-CPA ester and the acid; recrystallization of the salt to substantial diastereomeric purity; and neutralizing the salt to afford the substantially enantiomerically pure 3-CPA ester.

11 Claims, No Drawings

PREPARATION OF 3-AMINO-3-CYCLOPROPYLPROPANOATE ESTERS

INTRODUCTION

This invention pertains to a process for preparing enantiomerically enriched 3-amino-3-cyclopropylpropanoate esters, i.e., esters of 3-amino-3-cyclopropylpropanoic acid (3-cyclopropylalanine esters or 3-CPA esters) including substantially enantiomerically pure (R) or (S)-3-CPA esters. More specifically, this invention pertains to a process for the preparation of substantially enantiomerically pure 3-CPA esters by a 5-step process wherein cyclopropanecarboxaldehyde (CPCA) is reacted with malonic acid and a source of ammonia to obtain β-cyclopropylalanine (3-CPA); esterifying the 3-CPA; contacting the 3-CPA ester with a substantially enantiomerically pure acid selected from tartaric acid, dibenzoyltartaric acid and mandelic acid to obtain a diastereomeric salt of the 3-CPA ester and the acid; recrystallizing the salt to afford a substantially diastereomerically pure salt; and neutralizing the salt to afford the substantially enantiomerically pure 3-CPA ester.

3-Amino acids are an important class of organic compounds and often are found in physiologically active compounds. See, for example, Suffness, Ed., Taxol® *Science and Applications* (CRC, Boca Raton, Fla., 1995) and Plattner, in *Annual reports in Medicinal Chemistry*, J. A. Bristol, Ed (Academic Press, San Diego, 1994), vol 29, pp. 113–22. Similarly, the cyclopropyl fragment also is found in pharmaceutical products. See, for example, British Patent Publication GB 1,136,214, U.S. Pat. No. 3,433,791, Published PCT Patent Application WO 9304047, Spanish Patent ES 539110, U.S. Pat. No. 4,863,918, Czech Patent CZ 279821 and European Patent Publication EP 0380312 A1.

Only one reference to an ester of a ∃-amino acid substrate of this type can be found in the literature and concerns the use of ethyl 3-amino-3-cyclopropylpropanoate in the synthesis of a platelet aggregation inhibitor, Published PCT Patent Application WO 9307867 A1 930429 (Application: WO 92-US8512). The racemic form of ethyl 3-amino-3-cyclopropylpropanoate was prepared by the action of diazomethane and palladium acetate on the corresponding vinyl compound, the preparation of which is not trivial.

BRIEF SUMMARY OF THE INVENTION

We have developed a process for the preparation of substantially enantiomerically pure (R) or (S) 3-CPA esters beginning with CPCA. Our novel process comprises the steps of:

(1) reacting CPCA with malonic acid and a source of ammonia in the presence of an inert solvent to obtain 3-cyclopropylalanine (3-CPA);
(2) contacting the 3-CPA with an alkanol in the presence of an acidic esterification catalyst to obtain a 3-CPA ester;
(3) contacting the 3-CPA ester with a substantially enantiomerically pure acid selected from tartaric acid, dibenzoyltartaric acid and mandelic acid to obtain a diastereomeric amine addition salt of the 3-CPA ester and the acid;
(4) recrystallizing the salt to afford a substantially diastereomerically pure amine addition salt of the 3-CPA ester and the acid; and
(5) neutralizing the salt with a base to afford a substantially enantiomerically pure 3-CPA ester.

As used herein, "substantially diastereomerically pure" refers to a compound possessing greater than 95% diastereomeric excess [de] wherein diastereomeric excess is defined as the percent of one diastereomer minus the percent of the other diastereomer. Similarly, "substantially enantiomerically pure" refers to a compound possessing greater than 95% enantiomeric excess [ee] wherein enantiomeric excess is defined as the percent of one enantiomer minus the percent of the other enantiomer In step (1) of the process, CPCA is contacted with malonic acid and a source of ammonia in the presence of an inert solvent. The ammonia source may be ammonia or an ammonium salt such as an ammonium halide, e.g., ammonium chloride, or an ammonium carboxylate, i.e., an ammonium salt of a mono- or di-carboxylic acid containing up to about 8 carbon atoms, e.g., ammonium acetate, ammonium citrate and ammonium oxalate. The inert solvent may be selected from various non-reactive materials which are liquid under the reaction conditions. Examples of such inert solvents include alkanols, hydrocarbons, ketones, water or mixture thereof. The solvent preferably is a $C_1$–$C_4$ alkanol, most preferably, ethanol.

Step (1) may be carried out at a temperature between room temperature and the boiling point of the solvent, preferably at about 20 to 120° C., most preferably at the boiling point of the solvent. Step (1) of the process described herein may be carried out at ambient pressures. However, pressures moderately below or above ambient pressure may be used. For example, increased pressure may be employed to limit the loss of ammonia from the reaction mixture and thus enhance the yield of the process. In particular, step (1) can be carried out using pressures in the range of about 1 to 100 atmospheres, preferably 1 to 30 atmospheres. The mole ratio of the CPCA and malonic acid may be in the range of about 0.10:1 to about 10:1, preferably in the range of about 0.5:1 to about 2:1. The mole ratio of the ammonia or ammonia source to CPCA may be in the range of about 1:1 to about 10:1, preferably in the range of about 2:1 to about 10:1. The 3-CPA product from step (1) may be isolated by standard isolation techniques such as filtration of the reaction mixture.

Step (2) of the process involves contacting the racemic 3-CPA from step (1) with a branched or unbranched alkanol, preferably a $C_1$–$C_4$ alkanol, most preferably isopropanol, in the presence of an acidic esterification agent or catalyst to produce an alkyl ester of 3-CPA. The acidic catalyst may be selected from various acidic materials such as thionyl chloride, hydrohalic acids, e.g., hydrogen chloride, sulphonic acids, e.g., methanesulphonic acid, benzenesulphonic acid, toluenesulphonic acid, and the polymer-bound sulphonic acids derived from vinylbenzenesulphonic acid and divinylbenzene; or a phosphoric acid. Thionyl chloride is the preferred acidic catalyst for step (2). Step (2) of the process may be carried out at a temperature in the range of from room temperature to the boiling point of the solvent, preferably at about 50 to 120° C., most preferably at the boiling point of the solvent.

In step (3) of our novel process the racemic amino ester from step (2) is contacted with an enantiomerically-enriched acid selected from comprising tartaric acid, dibenzoyltartaric acid or mandelic acid, preferably enantiomerically-enriched tartaric acid, in the presence of an inert solvent to obtain a diastereomeric salt of the ester. The mole ratio of the 3-CPA ester to the enantiomerically-enriched acid used in step (3) may be in the range of about 1.5:1 to about 3:1, most preferably about 2:1. The inert solvent may be selected from various non-reactive materials such as, for example, branched or unbranched alkanols, ethers, ketones, water or a mixture thereof. Preferred solvents comprise $C_1$–$C_4$ alkanols and mixtures thereof with water, especially isopropanol/water mixtures, e.g., a 9:1 by volume ratio isopropanol:water mixture. Step (3) may be carried out at a temperature of from room temperature to the boiling point of the solvent, preferably at about 50 to 120° C., most preferably at the boiling point of the solvent. Upon cooling the reaction mixture to room temperature, the enantiomerically-enriched salt of the 3-CPA ester may be recovered by filtration.

Step (4) of the process involves recrystallization from the same solvent mixture to afford a substantially diastereomerically pure amine addition salt of the 3-CPA ester with the substantially enantiomerically pure acid. The substantially diastereomerically pure salt produced by the 4-step process is an amine addition salt of the 3-CPA ester and the enantiomerically-enriched tartaric acid, dibenzoyltartaric acid or mandelic acid. These substantially diastereomerically pure amine addition salts of the 3-CPA esters are novel compositions of matter.

The substantially diastereomerically pure salt produced in step (4) is contacted in step (5) with an aqueous base in the presence of an inert water-immiscible solvent to convert the salt to the substantially enantiomerically pure 3-CPA ester, i.e., the free amine. The base may be selected from one or more of the hydroxides, carbonates and/or bicarbonates of the alkali metals and/or alkaline earth metals. Sodium and potassium hydroxides represent the preferred bases. The inert solvent may be selected from a wide variety of non-reactive materials such as ethers, esters, hydrocarbons, chlorinated hydrocarbons, water or mixture thereof. The amount of base used preferably is between 2 and 5 molar equivalents based on moles of salt. The temperature of the reaction is preferably between 5 and 25° C. to minimize hydrolysis of the 3-CPA ester.

The substantially enantiomerically pure 3-CPA ester produced in step (5) may be hydrolyzed in a step (6) to the corresponding substantially enantiomerically pure 3-CPA, i.e., the acid, by contacting the amino ester with aqueous solution of an acid or a base in an inert solvent. Examples of suitable acids include mineral acids such as hydrohalic acids such as hydrochloric and hydrobromic acids; sulfuric acid; phosphoric acid; and alkyl- and arylsulphonic acids such as methanesulphonic, benzenesulphonic and toluenesulphonic acids. The acid preferably is hydrochloric acid. The acid:amino ester mole ratio may be in the range of about 1:1 to 10:1. The base may comprise an alkali metal or alkali earth metal hydroxide in a base:amino ester mole ratio of about 1:1 to 10:1. The inert solvent may be any non-reactive solvent such as an ether, aromatic or aliphatic hydrocarbon, ketone, water or a mixture thereof. Step (6) may be carried out at a temperature of about room temperature to the boiling point of the solvent, preferably at the boiling point of the solvent. The reaction product produced by step (6) is the acid addition salt of 3-CPA, e.g., the hydrochloride or sulfate. Both the racemic and substantially diastereomerically pure 3-CPA and the acid addition salts thereof are novel compositions of matter.

The operation of the process provided by our invention is further illustrated by the following example. The identities of the products obtained were confirmed by nuclear magnetic resonance spectrometry, mass spectrometry and infrared spectrometry. The percentages specified in the examples are by weight unless otherwise specified.

EXAMPLE 1

Cyclopropanecarboxaldehyde (CPCA, 200 g, 2.85 mol) was dissolved in ethanol (1 L, 5 vol) and ammonium acetate (439.9 g, 5.71 mol) added, with stirring. The resulting solution was stirred at room temperature for 1 hour. After the addition of malonic acid (297.1 g, 2.85 mol), the reaction mixture was stirred overnight at room temperature, then heated at reflux for 6 hours. After cooling to 30° C., acetone (2 L, 10 vol) was added and the reaction mixture was stirred overnight at room temperature. The yellow mixture was cooled in an ice bath with stirring for 30 minutes. After filtering, the white solid was washed with ice-cold acetone (2×200 mL, 1 vol) and dried on the filter paper and then in a vacuum oven to give the racemic 3-CPA (236 g, 64% yield).

The racemic 3-CPA prepared according to the preceding paragraph (100 g, 0.77 mol) was dissolved in isopropanol (1 L, 10 vol) and cooled in an ice bath with stirring for 20 minutes. After adding drop-wise thionyl chloride (80.54 mL, 1.16 mol), the mixture was warmed to 50° C. for 6 hours. After cooling to room temperature, the volatiles were evaporated in vacuo and 4M sodium hydroxide was added to adjust the pH of the reaction mixture to 14. The aqueous layer was extracted with dichloromethane (3×1 L, 10 vol) and the extracts were dried over magnesium sulfate and filtered. The filtrates were combined and evaporation of volatiles in vacuo gave the 3-CPA 2-propyl ester as a yellow oil. The crude 3-CPA ester was purified by distillation (80° C., 4.5 mbar) to give a colourless oil (99.71 g, 75% yield).

The pure racemic 3-CPA 2-propyl ester from the procedure of the preceding paragraph (10 g, 0.058 mol) was added to a mixture of L-tartaric acid (4.38 g, 0.029 mol) in a solvent mixture of isopropanol (45 mL, 4.5 vol) and water (5 mL, 0.5 vol). The heterogeneous mixture was stirred and heated to reflux until completely dissolved. The reaction mixture then was cooled to room temperature and stirred overnight. The yellow mixture was cooled in an ice bath with stirring for 30 minutes. The precipitate was collected by filtration and was washed with an ice-cold solvent mixture of isopropanol (9 mL, 0.9 vol) and water (1 mL, 0.1 vol). Drying on the filter paper and then in a vacuum oven, gave a 2:1 3-CPA 2-propyl ester:tartaric acid salt (7 g, 98% yield, 74% ee by HPLC) The tartaric acid salt (7 g, 0.01 mol) was suspended in a solvent mixture of isopropanol (31.5 mL, 4.5 vol) and water (3.5 mL, 0.5 vol). The heterogeneous mixture was heated to reflux until completely dissolved and then cooled down to room temperature. The reaction mixture was stirred overnight. After cooling down in an ice bath for 30 minutes and then filtering, the solid was washed with an ice cold solvent mixture of isopropanol (9 mL, 0.9 vol) and water (7 mL, 1 vol). Drying on the filter paper and then in a vacuum oven gave a purified 2:1 amino ester:tartaric acid salt (5.43 g, 76% yield, 98.3% ee by HPLC).

The salt (5.43 g) from the preceding paragraph was dissolved in a dichloromethane:2M aqueous NaOH (5 mL:5 mL) mixture and stirred vigorously. The phases were separated and the organic phase washed again with 2M aqueous NaOH (3 mL), dried over magnesium sulphate and the solvent removed in vacuo to give the substantially enantiomerically pure 3-CPA 2-propyl ester as a clear oil (3.36 g, 99% yield).

To the amino ester (20 g, 0.12 mol), prepared in the previous paragraph, was added 3M HCl (60 mL, 3 vol) carefully with stirring. The reaction mixture was then heated to 115° C. (oil bath), and the isopropanol was distilled off over 1.5 hours. Toluene (60 mL, 3 vol) was then added to the reaction mixture, the temperature of the oil bath was increased to 125° C., and the water was removed azeotropically over about 2 hours (53 mL of water was collected). After cooling the mixture to 60° C. acetone (40 mL, 2 vol) was added, and the resulting slurry was stirred vigorously for 30 minutes. The white solid then was collected by filtration and was washed with acetone (2×40 mL, 2×2 vol) and then dried, yielding the HCl salt of the desired 3-CPA (17.7 g, 91% of theory).

The invention has been described in detail with particular reference to preferred embodiments thereof, but it will be understood that variations and modifications can be effected within the spirit and scope of the invention.

We claim:

1. Process which comprises the steps of:
   (1) reacting cyclopropanecarboxaldehyde with malonic acid and a source of ammonia in the presence of an inert solvent to obtain 3-amino-3-cyclopropylpropanoic acid;
   (2) contacting the 3-amino-3-cyclopropylpropanoic acid with an alkanol in the presence of an acidic esterification catalyst to obtain a 3-amino-3-cyclopropylpropanoate ester; and
   (3) contacting the 3-amino-3-cyclopropylpropanoate ester with an enantiomerically-enriched acid selected from tartaric acid, dibenzoyltartaric acid and mandelic acid to obtain a diastereomeric amine salt of the 3-amino-3-cyclopropylpropanoate ester and the acid;
   (4) recrystallizing the salt to afford a substantially diastereomerically pure addition salt of the 3-amino-3-cyclopropylpropanoate ester and the acid, and
   (5) neutralizing the substantially diastereomerically pure addition salt to afford the substantially enantiomerically pure 3-amino-3-cyclopropylpropanoate ester.

2. Process according to claim 1 which comprises reacting cyclopropanecarboxaldehyde with malonic acid and a source of ammonia selected from ammonia and ammonium salts selected from ammonium halides and ammonium carboxylates at a temperature of about 20 to 120° C. in the presence of an inert solvent selected from $C_1$–$C_4$ alkanol.

3. Process according to claim 1 wherein step (2) comprises contacting the 3-amino-3-cyclopropylpropanoic acid with a $C_1$–$C_4$ alkanol in the presence of an acidic esterification agent selected from thionyl chloride, hydrohalic acids, sulphonic acids and phosphoric acid at a temperature of about 50 to 120° C.

4. Process according to claim 1 wherein step (3) comprises contacting the 3-amino-3-cyclopropylpropanoate ester with a substantially enantiomerically pure acid selected from tartaric acid, dibenzoyltartaric acid and mandelic acid in the presence of an inert solvent selected from $C_1$–$C_4$ alkanols and mixtures thereof with water.

5. Process according to claim 1 which includes the step of (6) contacting the 3-amino-3-cyclopropylpropanoate ester produced in step (5) with an acid or a base in an inert solvent to hydrolyze the 3-amino-3-cyclopropylpropanoate ester to the corresponding 3-amino-3-cyclopropylpropanoic acid.

6. A diastereomeric amine salt of an alkyl ester of 3-amino-3-cyclopropylpropanoic acid comprising the 3-amino-3-cyclopropylpropanoate ester and an enantiomerically-enriched acid selected from tartaric acid, dibenzoyltartaric acid and mandelic.

7. A diastereomeric amine salt of a $C_1$–$C_4$ alkyl ester of 3-amino-3-cyclopropylpropanoic acid comprising the $C_1$–$C_4$ alkyl ester of 3-amino-3-cyclopropylpropanoic acid and enantiomerically-enriched tartaric acid.

8. 3-Amino-3-cyclopropylpropanoic acid and acid addition salts thereof.

9. An acid addition salt of 3-amino-3-cyclopropylpropanoic acid according to claim 8 wherein the acid is a hydrogen halide acid or sulfuric acid.

10. Substantially enantiomerically pure 3-amino-3-cyclopropylpropanoic acid and acid addition salts thereof.

11. An acid addition salt of substantially enantiomerically pure 3-amino-3-cyclopropylpropanoic acid according to claim 10 wherein the acid is a hydrogen halide acid or sulfuric acid.

* * * * *